(12) United States Patent
Laduca

(10) Patent No.: US 10,751,515 B2
(45) Date of Patent: Aug. 25, 2020

(54) HELICAL BALLOON CATHETER

(71) Applicant: QMAX, LLC, Santa Cruz, CA (US)

(72) Inventor: Robert C. Laduca, Santa Cruz, CA (US)

(73) Assignee: QMAX, LLC, Santa Cruz, CA (US)

( * ) Notice: Subject to any disclaimer, the term of this patent is extended or adjusted under 35 U.S.C. 154(b) by 775 days.

(21) Appl. No.: 15/574,112

(22) PCT Filed: Apr. 15, 2015

(86) PCT No.: PCT/US2015/026003
§ 371 (c)(1),
(2) Date: Nov. 14, 2017

(87) PCT Pub. No.: WO2015/160972
PCT Pub. Date: Oct. 22, 2015

(65) Prior Publication Data
US 2018/0344989 A1    Dec. 6, 2018

Related U.S. Application Data

(60) Provisional application No. 61/979,991, filed on Apr. 15, 2014.

(51) Int. Cl.
*A61M 25/10* (2013.01)
*A61M 25/09* (2006.01)
*A61M 25/01* (2006.01)

(52) U.S. Cl.
CPC .... *A61M 25/1002* (2013.01); *A61M 25/0155* (2013.01); *A61M 25/0147* (2013.01); *A61M 2025/09125* (2013.01); *A61M 2025/105* (2013.01); *A61M 2025/1095* (2013.01)

(58) Field of Classification Search
CPC ......... A61M 25/0155; A61M 25/0074; A61M 25/0147; A61M 25/1002; A61M 25/10185; A61M 25/0041; A61M 2025/105; A61M 2025/0163; A61M 25/1097; A61M 2210/12; A61M 2025/09125; A61M 2025/0155; A61F 2/958; A61F 2230/0091
See application file for complete search history.

(56) References Cited

U.S. PATENT DOCUMENTS

| | | | |
|---|---|---|---|
| 5,226,888 A * | 7/1993 | Arney | A61M 25/1002 604/103.07 |
| 6,183,491 B1 * | 2/2001 | Lulo | A61B 17/12022 606/191 |
| 6,482,221 B1 * | 11/2002 | Hebert | A61B 17/12022 606/194 |
| 6,679,860 B2 | 1/2004 | Stiger | |
| 7,081,115 B2 * | 7/2006 | Taimisto | A61B 18/1492 606/41 |
| 2002/0193735 A1 * | 12/2002 | Stiger | A61M 25/104 604/101.01 |
| 2004/0039372 A1 | 2/2004 | Carmody | |

(Continued)

FOREIGN PATENT DOCUMENTS

| | | |
|---|---|---|
| JP | 2011-169464 | 9/2011 |
| WO | WO 2014/055547 | 4/2014 |

*Primary Examiner* — Jenna Zhang
(74) *Attorney, Agent, or Firm* — Levine Bagade Han LLP

(57) ABSTRACT

Methods and devices described for improved catheters including those having a deflectable section to allow for expansion while maintaining flow through a vessel.

20 Claims, 21 Drawing Sheets

(56) References Cited

U.S. PATENT DOCUMENTS

| | | | |
|---|---|---|---|
| 2009/0326550 A1* | 12/2009 | Drake | A61N 1/059 606/129 |
| 2011/0172697 A1* | 7/2011 | Jonsson | A61B 17/12036 606/194 |
| 2011/0230700 A1* | 9/2011 | Sing | A61N 5/1015 600/7 |
| 2012/0116382 A1* | 5/2012 | Ku | A61M 25/0074 606/33 |
| 2015/0306358 A1* | 10/2015 | Duffy | A61F 2/95 623/1.11 |

* cited by examiner

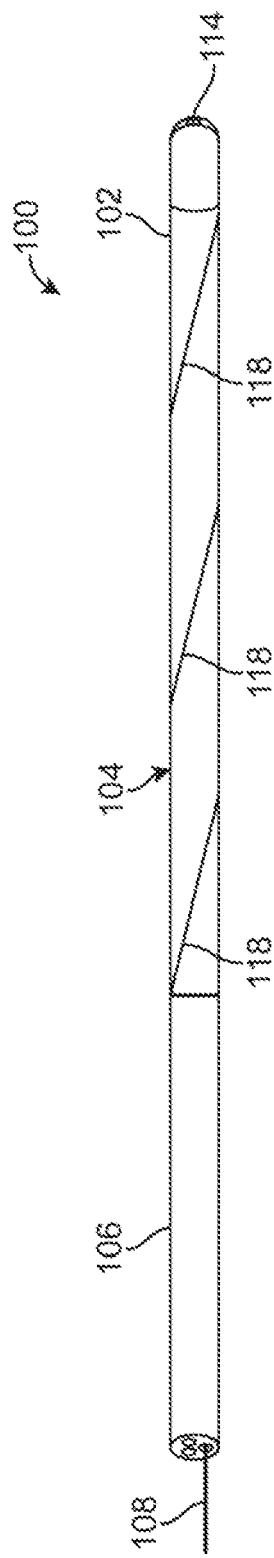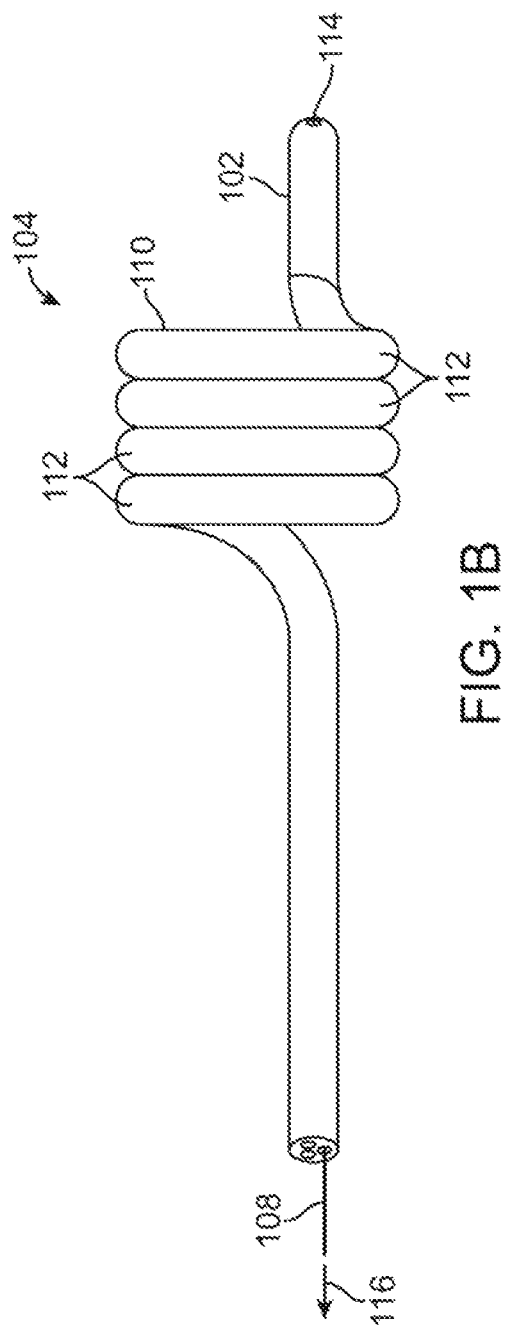
FIG. 1A
FIG. 1B

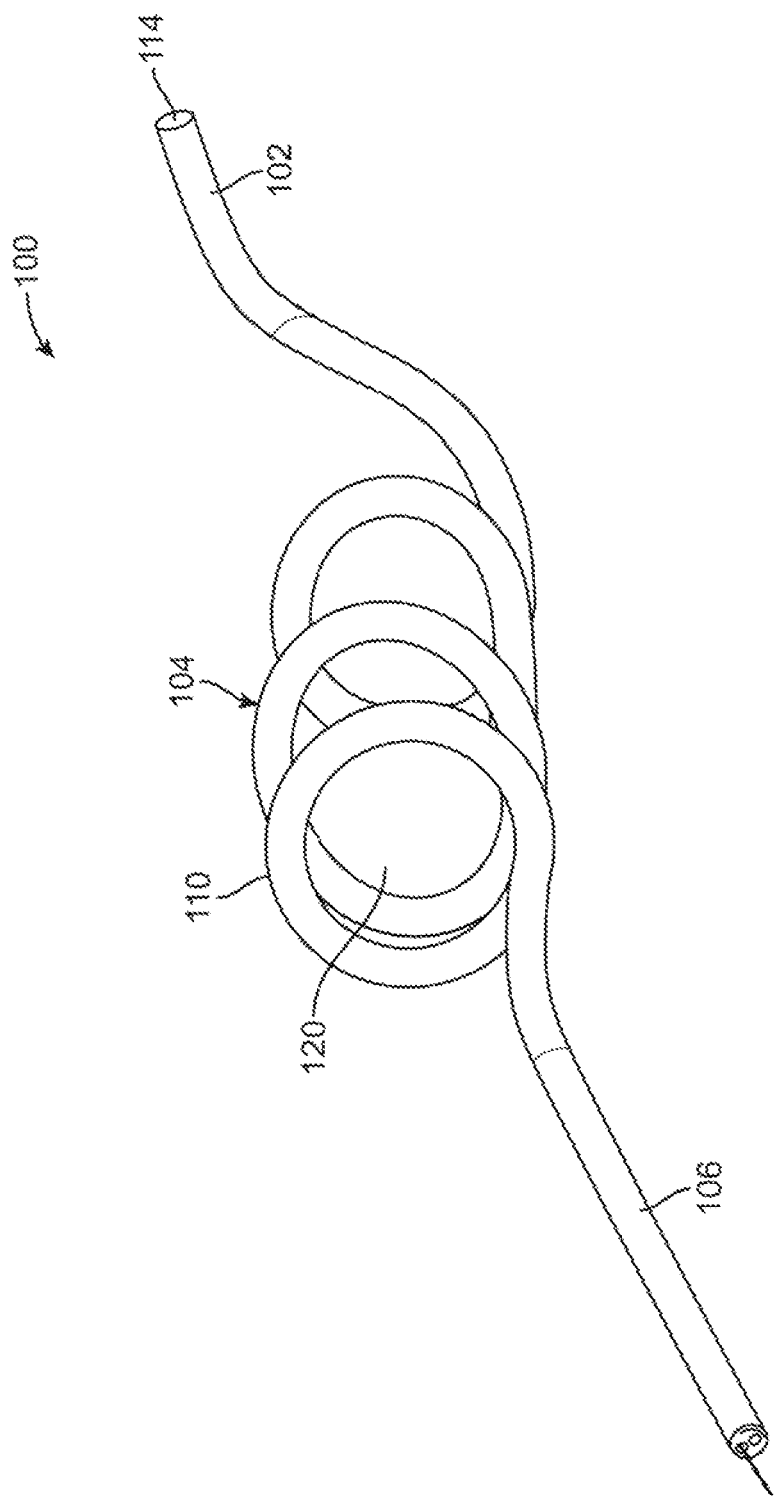

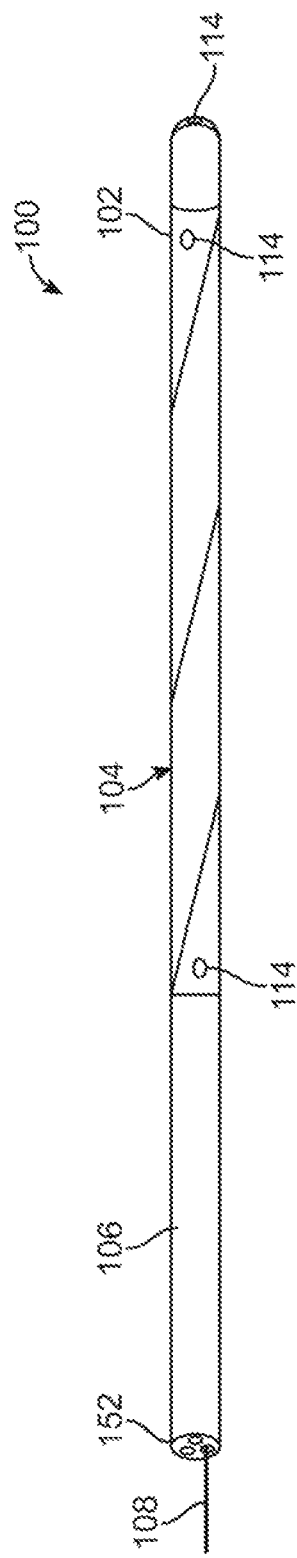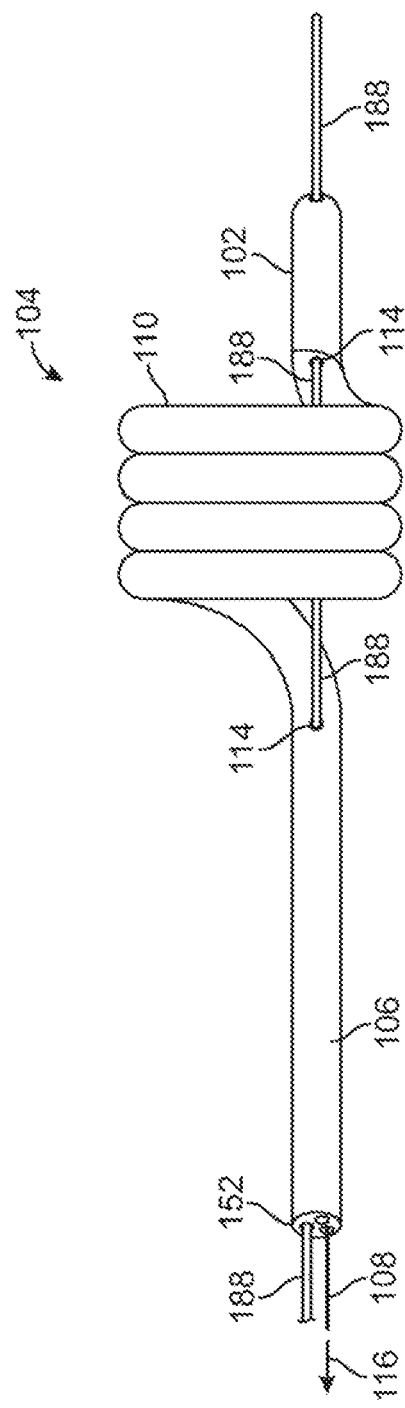

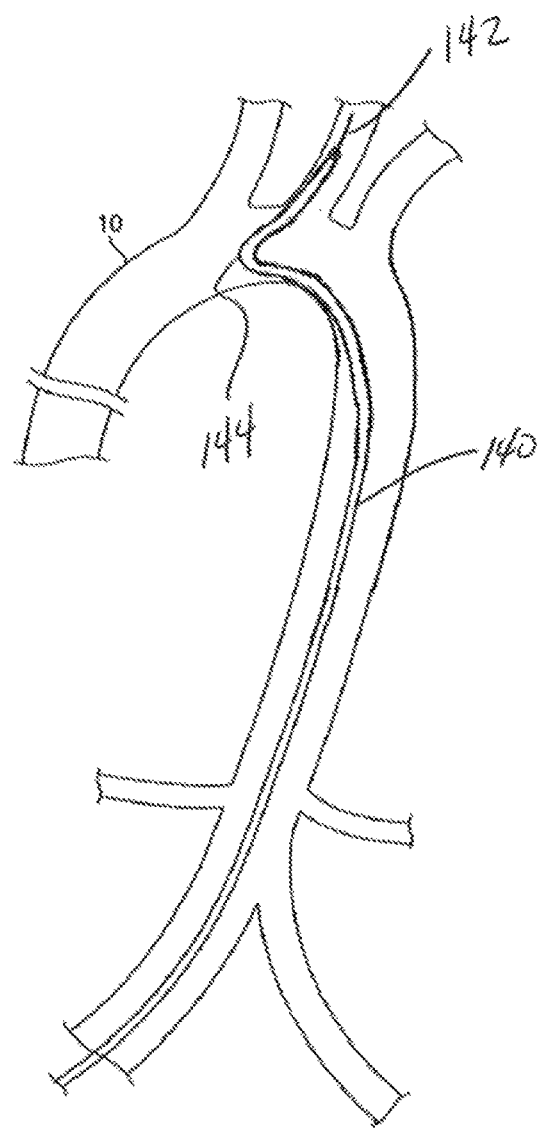
Fig. 13A
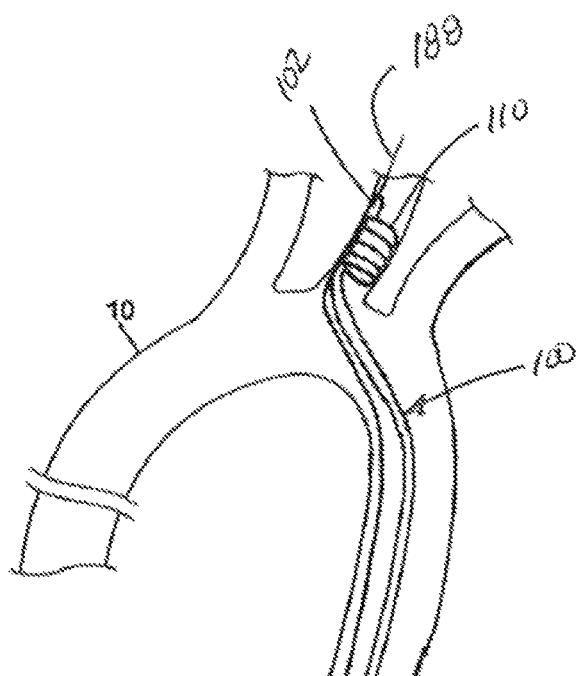
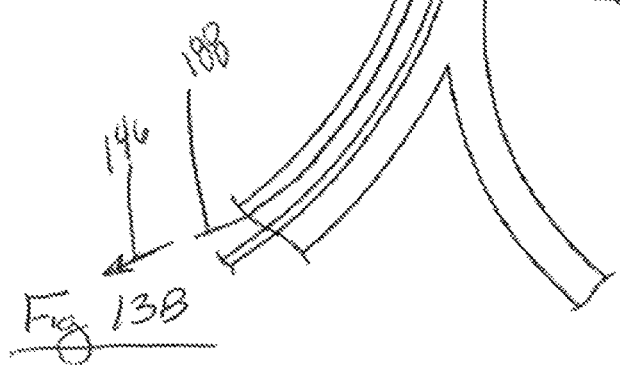
Fig. 13B

HELICAL BALLOON CATHETER

RELATED APPLICATION

This application is a national stage application under 35 U.S.C. 371 of U.S. International Application No. PCT/US2015/026003 filed Apr. 15, 2015, which claims benefit of U.S. Provisional Application No. 61/979,991 filed Apr. 15, 2014, which is related to U.S. application Ser. No. 14/043,608 filed Oct. 1, 2013 and is related to U.S. Provisional Applications 61/734,860 filed on Dec. 7, 2012; U.S. Provisional Application 61/724,875 filed on Nov. 9, 2012; and U.S. Provisional Application 61/708,524 filed on Oct. 1, 2012. The entirety of each of which is incorporated by reference herein.

BACKGROUND OF THE INVENTION

There remains a need for a balloon catheter that can be deployed to provide a radial outward force against a body lumen wall without causing occlusion of the body lumen. Such a catheter can be constructed to provide varying expansive characteristics such as a low or high radial outward force, a low or high ratio of expansion, as well as provide the ability to navigate through tortuous anatomy.

SUMMARY

Methods and devices described herein provide for improved catheters including those having a deflectable section to allow for expansion while maintaining flow through a vessel. While the following disclosure discusses devices and methods for use in body vessels, such methods and devices can be applied to various body portions.

The present disclosure includes catheters having a proximal portion, distal portion, and a deflectable section located therebetween, the deflectable section having a deflectable cross section; where the deflectable section cross section comprises an elastic material on a first side and a flexible support material on a second side, an inflation lumen bounded by both the elastic material and the flexible support material, and where the deflectable section cross section rotates along a length of the deflectable section such that the elastic material, inflation lumen and flexible support material extend helically along the length of the deflectable section; a pull wire extending through the flexible support material at least along the length of the deflectable section and at least to the proximal portion of the catheter, such that proximal tension applied to the pull wire causes the deflectable section to deflect into a helical profile; and wherein when a pressure within the inflation lumen increases, the elastic material expands away from the inflation lumen.

In one variation, the helical profile the flexible support material is located along an internal diameter of the helical profile and the elastic material is located on an external diameter of the helical profile such that upon increasing the pressure within the inflation lumen the elastic material expands radially outward from the helical profile.

In another variation, the pull wire extends through a pull wire lumen and where the pull wire lumen and inflation lumen are located 180 degrees opposite in the deflectable section cross section.

Variations of the devices can include a guidewire lumen extending through the proximal portion and flexible support material of the deflectable section. The devices can also optionally include one or more guidewire lumens that extend through a center of the proximal portion, distal portion, and the deflectable section.

In one example, the guidewire lumen extends through the distal portion.

The devices can also optionally include an inflation lumen that extends through the proximal portion.

In variations of the device, a flexible support material durometer is less than a proximal portion durometer.

The devices can include helical deflectable sections having at least one turn or a plurality of turns where the helical profile has a pitch and a diameter.

The devices can include variations where at least two turns of the plurality of turns is contiguous along a length of the helical profile. In additional variations, at least two turns of the plurality of turns are spaced and do not touch along a length of the helical profile.

In some variations, where the pitch of the helical profile is consistent for the plurality of turns. Alternatively, the pitch of the helical profile can vary for the plurality of turns. Furthermore, the diameter of the helical profile can be consistent along a length of the helical profile or can vary.

The present disclosure also includes methods for performing a medical procedure within a body lumen. In one example such a method includes advancing a catheter into the body lumen, the catheter having a proximal portion, distal portion, and a deflectable section located therebetween, where a deflectable section cross section comprises an elastic material on a first side and a flexible support material on a second side, an inflation lumen bounded by both the elastic material and the flexible support material, and where the deflectable section cross section rotates along a length of the deflectable section such that the elastic material, inflation lumen and flexible support material extend helically along the length of the deflectable section; converting the deflectable section from a near linear shape to a helical shape by applying tension to a pull wire extending through the flexible support material at least along the length of the deflectable section and at least to the proximal portion of the catheter, such that tension in the pull wire causes the deflectable section to deflect into the helical shape; and expanding the elastic material by increasing a pressure within the inflation.

In another example, the method includes expanding the elastic material by expanding the elastic material against a wall of the body lumen to apply an outward radial force on the wall of the body lumen, while allowing a passage through the helical shape such that the body lumen is not occluded by the catheter.

In another example, the method can include positioning the deflectable section of the catheter within a second medical device, and where expanding the elastic material causes the second medical device to expand against a wall of the body lumen while allowing a passage through the helical shape such that the body lumen is not occluded by the catheter.

The present disclosure also includes another variation of a catheter having a proximal portion, distal portion, and a deflectable section located therebetween; where a deflectable section cross section comprises an elastic material on a first side and a flexible support material on a second side, an inflation lumen bounded by both the elastic material and the flexible support material, and where the deflectable section cross section has two materials with different Young's modulus along a length of the deflectable section such that the elastic material, inflation lumen and flexible support materials change lengths at different rates during the inflation of the elastic portion of the tubing with the elastic balloon material elongating relative to the flexible support material of the catheter lumen which deflects the deflectable section into a coiled or helical shape that is; cylindrical cone or hooked shaped;

Such a Young's modulus can optionally be determined by $$F = -\frac{EA_0 \Delta L}{L_0}$$

Variations of the access device and procedures described herein include combinations of features of the various embodiments or combination of the embodiments themselves wherever possible.

BRIEF DESCRIPTION OF THE SEVERAL VIEWS OF THE DRAWINGS

FIG. 1A illustrates a catheter having a deformable section that can assume a helical configuration.

FIG. 1B illustrates a proximal force applied to a pull wire to cause the deflectable section to assume a helix or helical profile.

FIG. 1C shows a perspective view of a catheter that is in the helical configuration.

FIGS. 6A and 6B show a variation of the device where a guidewire lumen exits at one side of the deflectable section and reenters the device at a distal section.

FIGS. 13A and 13B illustrate a catheter backing out of a target location and an improved helical balloon catheter respectively.

DETAILED DESCRIPTION OF THE INVENTION

Figure 1D:
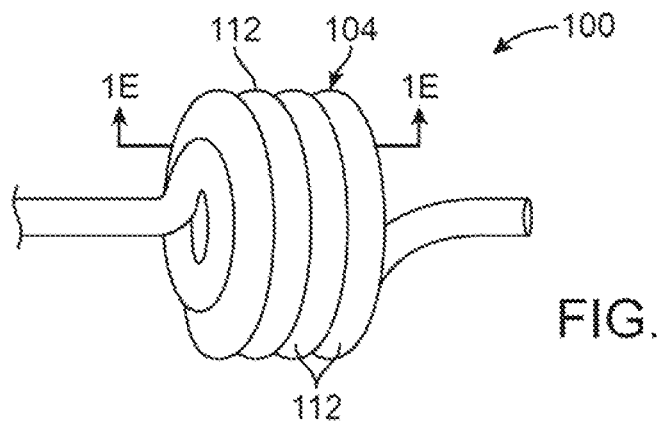
FIGS. 1D to 1H illustrate an expandable configuration of the catheter's deflectable section.

The following illustrations demonstrate various embodiments and examples of the devices and methods according to the present disclosure. Combinations of aspects of the various devices and methods or combinations of the devices and methods themselves are considered to be within the scope of this disclosure.

FIG. 1A illustrates a variation of a catheter 100 according to the present disclosure. FIG. 1A depicts the catheter 100 in a generally linear configuration; however, the catheter 100 can optionally be configured to be flexible to navigate through tortuous anatomy such as the vasculature and/or other organs throughout the body. FIG. 1A shows the catheter including a distal portion 102 having an optional lumen terminating at a distal end 114. The catheter 100 also includes a proximal portion 106 that is used by an operator to manipulate the catheter 100. Variations of the catheter 100 can include any number of hubs or handles located towards the proximal end of the proximal portion 106. The catheter 100 includes a deflectable section 104 located between the proximal portion 106 and distal portion 102. As discussed below, the deflectable section 104 can be actuated by a user via a pull wire 108 or other similar means. Variations of the device 100 can include a catheter 100 without a distal portion 102 or with a deflectable section 104 that extends along a significant length of the catheter 100. The deflectable section 104, as described in detail below, includes a cross section that rotates along a length of the deflectable section 104 and as depicted by 118. The rotated cross section comprises at least two different materials that extend helically along a length of the deflectable section 104.

FIG. 1B illustrates a proximal force 116 applied to the pull wire 108 to cause the deflectable section 104 to assume a helix or helical profile 110. The rotated cross section of the deflectable section 104 results in the helical deflection of the deflectable section 104 upon application of a tensile force on the pull wire 108 that extends through at least a portion of the deflectable section. The variation illustrated in FIG. 1B demonstrates a helical shape 100 having 4 turns 112. However, the devices and methods described herein can include any number of turns 112 as well as alternate helical configurations as shown below, FIG. 1C shows a perspective view of a catheter 100 having a deflectable section 104 in a helical profile, as shown the helical profile 110 includes a passage 120 that prevents the catheter 100 from occluding the body lumen when in a helical configuration.

Figure 1E:
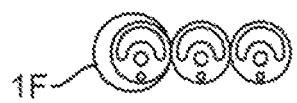
Figure 1F:
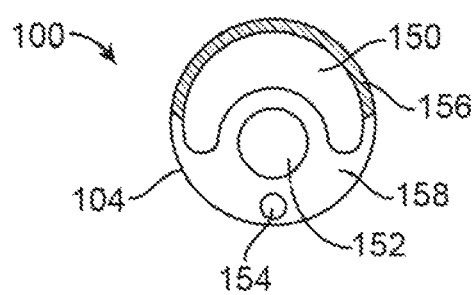

FIG. 1D illustrates another variation of a catheter 100 under the present disclosure. In this variation, the deflectable section 104 of the catheter 100 can expand. FIG. 1E illustrates a cross sectional view taken along the line 1E-1E in FIG. 1D FIG. 1F illustrates a magnified view of the left most turn 112 of hilical profile. As shown, the catheter 100 can include an inflation lumen 150, a guide wire lumen 152, and a pull wire 154 or pull wire lumen 154. A variation of the device includes an inflation lumen 150 that is bounded by an expandable material 156 and a flexible material 158. The flexible material allows for selective flexing of the deformable section 104 while the expandable material 156 expands upon pressurization of the inflation lumen 150. In certain variations, the elastic material 156 is oriented such that the material 156 expands outwardly from the helical shape while maintaining the passage 120 so that flow remains through the organ or body lumen.

The elastic material can comprise a material commonly used in medical elastic balloon. Examples of materials for the supportielastic material can include pebax or a mix of pebax and siloxane. The elastic material can be co-extruded with the flexible material. Also, variations of the device can include a proximal portion that comprises a stiffer material than the flexible material used in the deflectable section.

Furthermore, in certain variations, the device can automatically coil without the need for a separate pull wire given a specific selection of materials. For example, in such a variation the elastic expandable balloon material is co-extruded or otherwise bonded to a non-elastic material of the catheter and the two materials will have a different stiffness and elongation stress strain curves. In such a variation, upon inflation of the elastic portion of the tube, since the length changes on only one wall of the tubing, the other wall is constrainted by the less elastic material. This results in the balloon segment of the catheter automatically forming a helical coiled configuration upon expansion. The diameter of the balloon and the diameter of the inflated helical balloon configuration can be pre-determined by selecting the appropriate design parameters, including material selection, durometers, length, and extrusion cross sectional profiles.

Figure 1G:
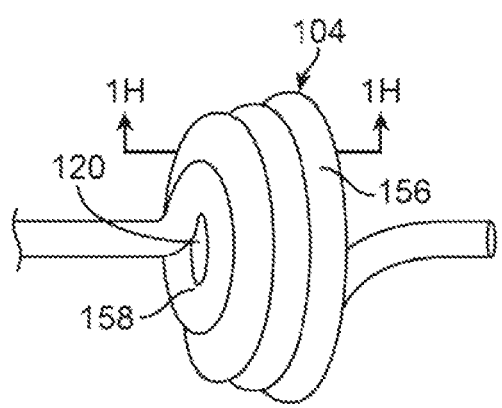

FIG. 1G illustrates expansion along the deformable section 104 by expanding the elastic material 156 in a direction away from the helical shape. As shown, the flexible material 158 allows for formation of the helical shape but prevents occlusion of the passage 120.

Figure 1H:
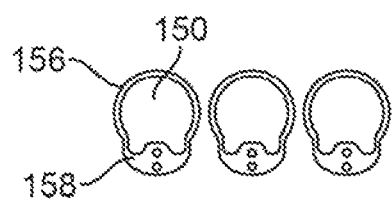

FIG. 1H shows a cross sectional view taken along the line 1H-1H in FIG. 1G. As shown, the elastic material 156 expands away from the helix because the inflation lumen is pressurized (either via a fluid or a gas). FIG. 1H also illustrates the elastic material 158 as allowing for deformation of the deflectable section 104 but also providing a support for the flexible material 156 to expand.

Figure 2A:
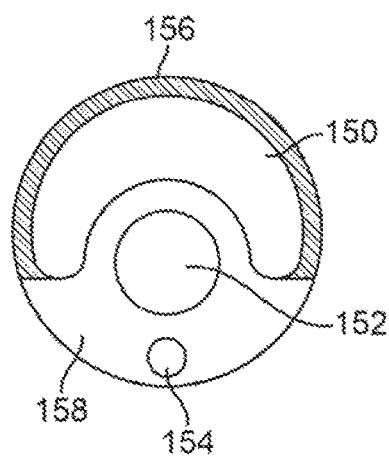
FIGS. 2A to 2K show how a cross section of the deflectable section rotates along a length of the deflectable section.

FIG. 2A illustrates a cross section of the deformable section 104 as shown in FIG. 1F. Again, the inflation lumen 150 is bounded by an expandable material 156 and the flexible material 158. The flexible material allows for selective flexing of the deformable section 104 while the expandable material 156 expands upon pressurization of the inflation lumen 150. Again, the elastic material 156 can be oriented such that the material 156 expands outwardly from the helical shape while maintaining the passage 120 so that flow remains through the organ or body lumen.

In one example, the non-expandable portion of the device can be fabricated from Peba, Polyurethane, Nylon or a blend of Polyurethane and Siloxane, or Peba and Siloxane, or Nylon and Siloxane. In the variations comprising Peba and Siloxane or Polvtirethan and Siloxane, or Nylon and Siloxane, the extrusion is processed such that Siloxane is uniformly dispersed through theother material. By having uniform disbursement of the Siloxane allows for uniform increased lubricity throughout the extrusion. Alternate variations include a device fabricated from an commonly known material used in medical device applications.

Figure 2B:
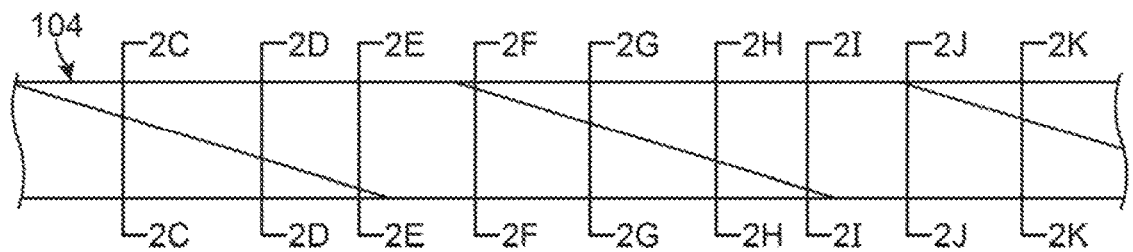
Figure 2C:
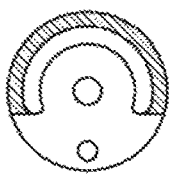
Figure 2D:
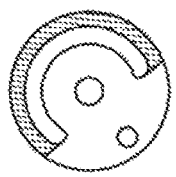
Figure 2E:
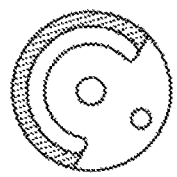
Figure 2F:
Figure 2G:
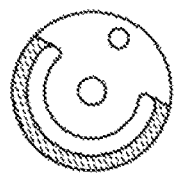
Figure 2H:
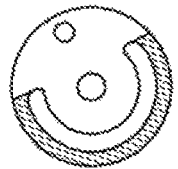
Figure 2I:
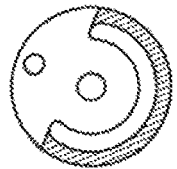
Figure 2J:
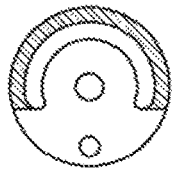
Figure 2K:
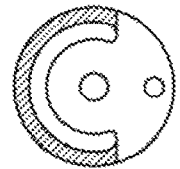

FIG. 2B shows a partial view of a deformable section 104 to illustrate the rotation of the cross section of the deformable section 104. FIG. 2B shows a number of cross sectional views taken along the lines 2C/2C through 2K/2K. As shown, the cross section rotates along a length of the deflectable section 104 such that the different materials forming the cross section helically rotate along the deflected portion 104. The rate of rotation and/or the length over which the cross section rotates can be selectively chosen to produce characteristics required for the particular application.

Figure 3A:
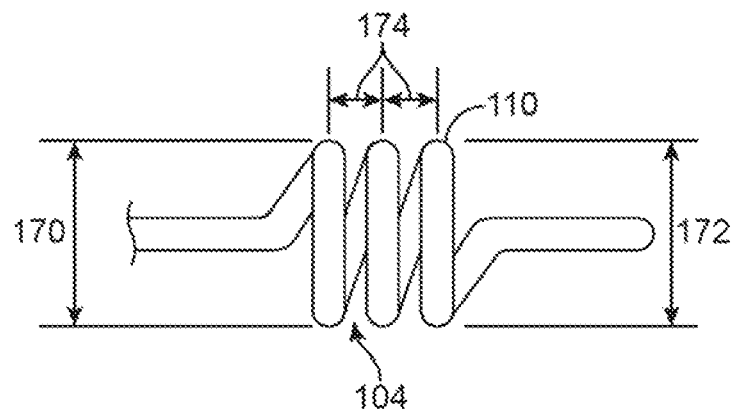
FIGS. 3A to 3C illustrate additional variations of the helical shapes for use with variations of catheters described herein.
Figure 3B:
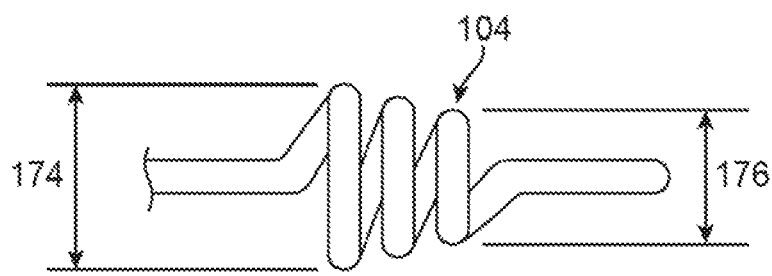
Figure 3C:
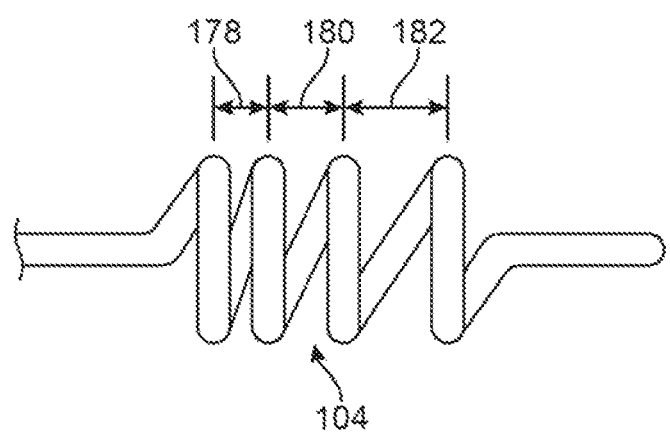

FIGS. 3A to 3C illustrate variations of the helical shape 110 of various deflectable sections 104. FIG. 3A illustrates a helical shape having a uniform diameter 170, 172 between the turns of the helix as well as a uniform pitch 174. FIG. 3B illustrates a varying diameter. In this example, the diameter 174 decreases in a distal direction such that the distal turn has a smaller diameter 176 than the proximal turn. FIG. 3C illustrates a helical shape having varying pitch as measured by distances 178, 180, 182. As shown, the pitch expands in a distal direction. However, the pitch can expand in a proximal direction as well.

Figure 4A:
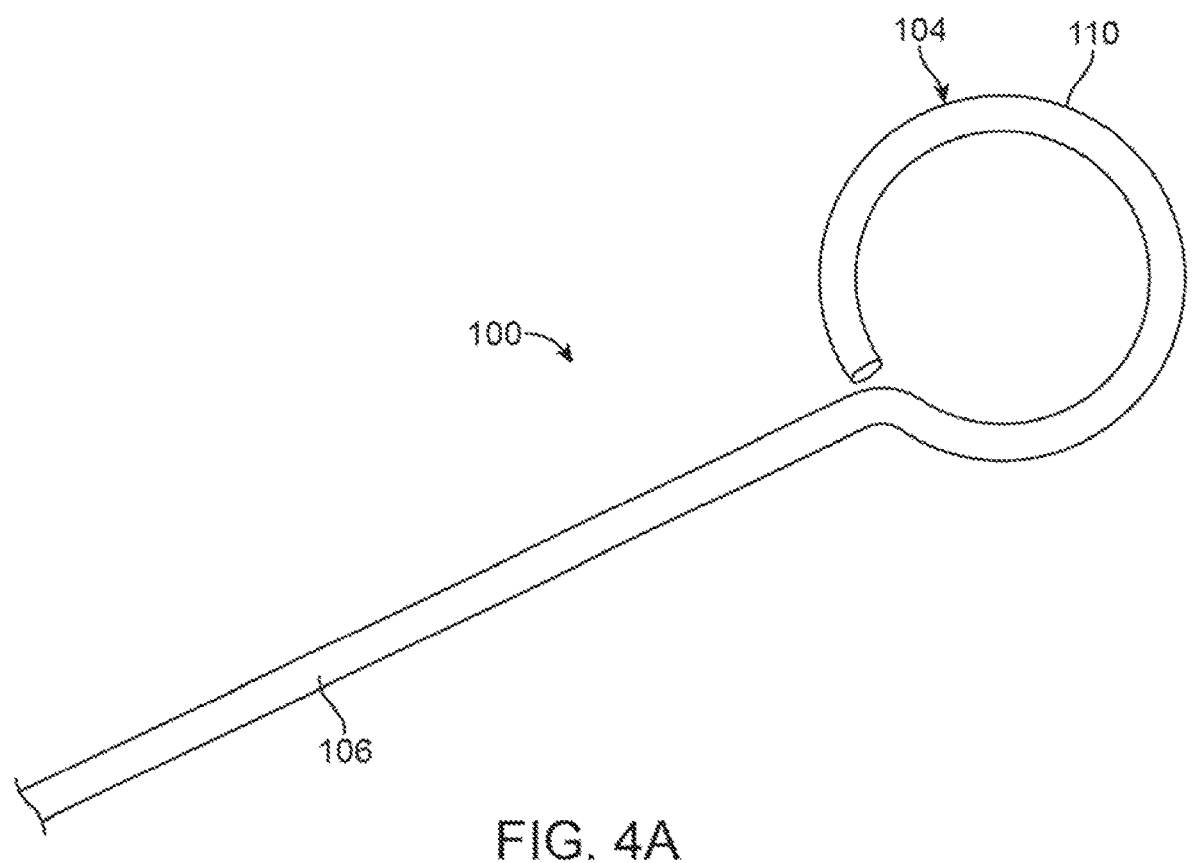
FIGS. 4A to 4C show a single turn catheter.
Figure 4B:
Figure 4C:
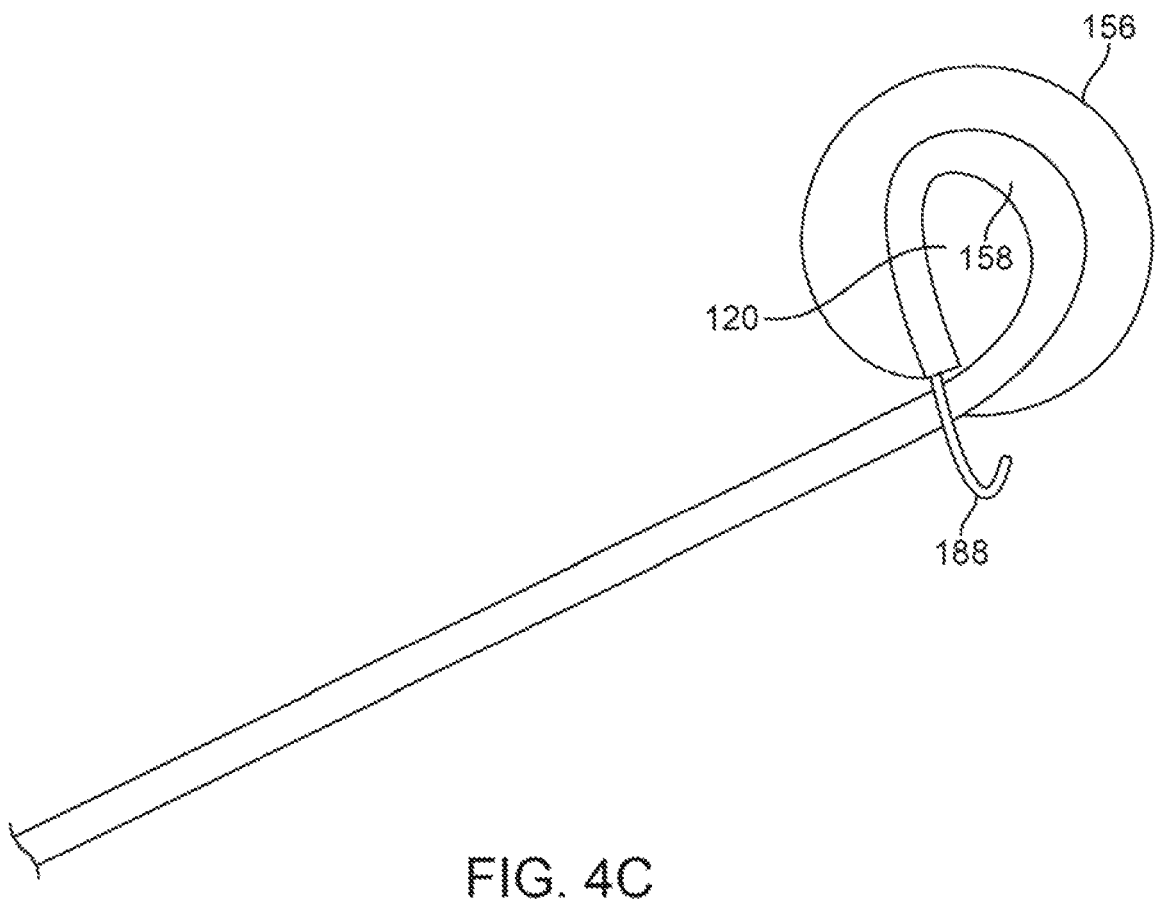

FIG. 4A illustrates a variation of a catheter 100 having a single helical turn 112, FIG. 4B illustrates a side view of the catheter 100 of FIG. 4A. FIG. 4C shows the variation of FIG. 4A upon expansion of the elastic material 156 while the flexible material 158 deforms to form the turn 112 and provide support to form die passage 120. FIG. 4C also shows a guidewire 188 being advanced through a guidewire lumen.

Figure 5A:
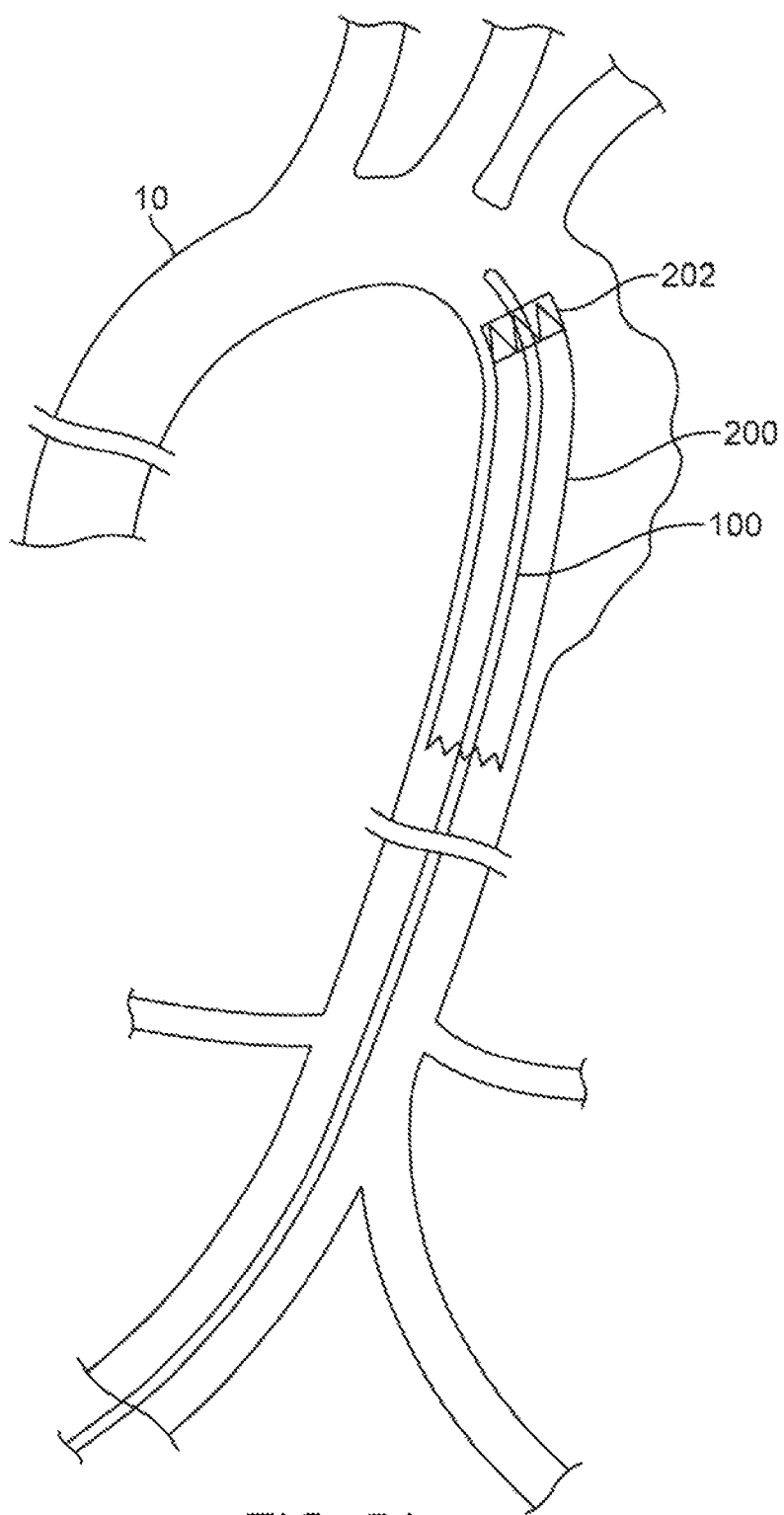
FIGS. 5A to 5C show an example of a catheter with a deformable section being used to deploy a medical device within a body lumen.
Figure 5B:
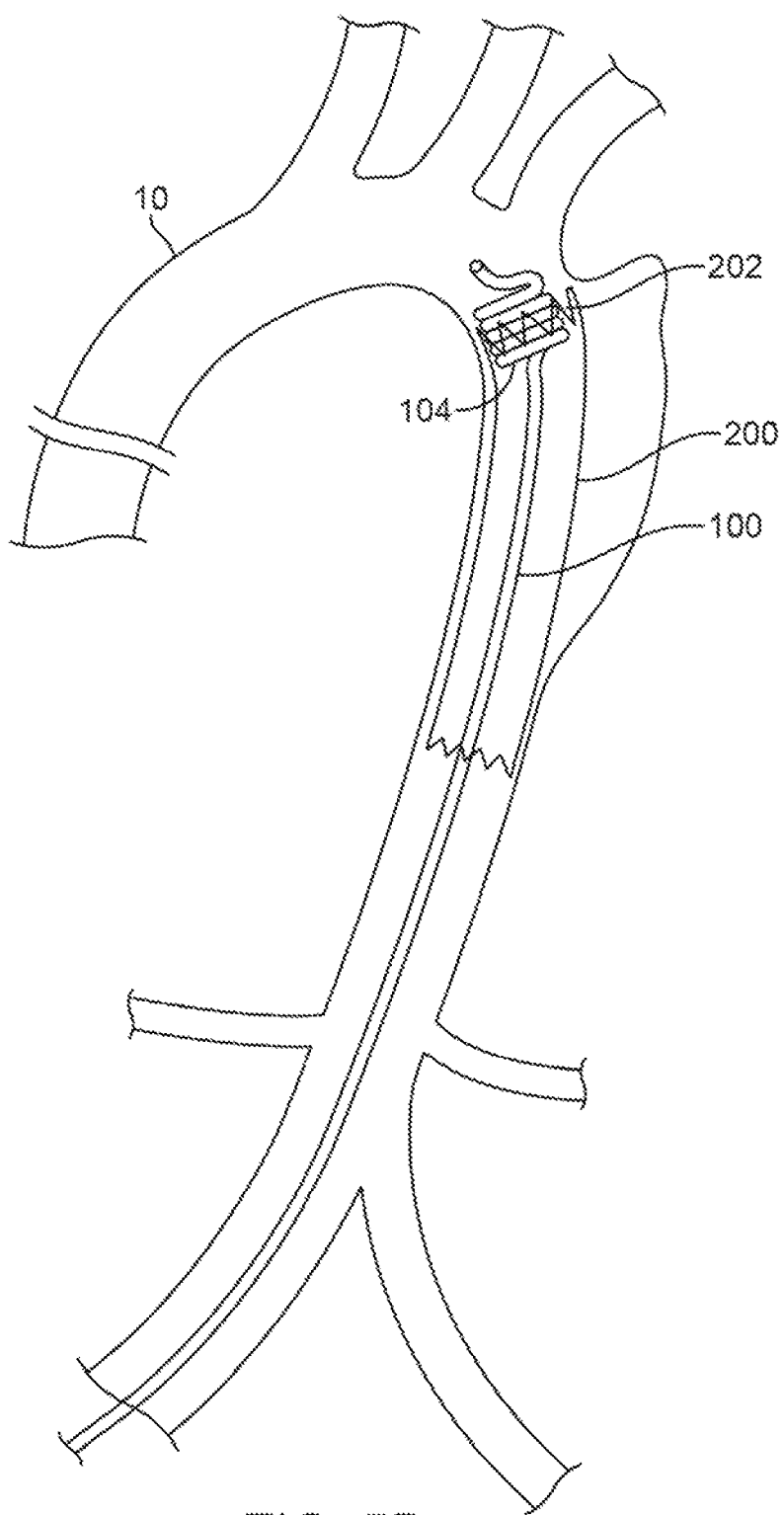
Figure 5C:
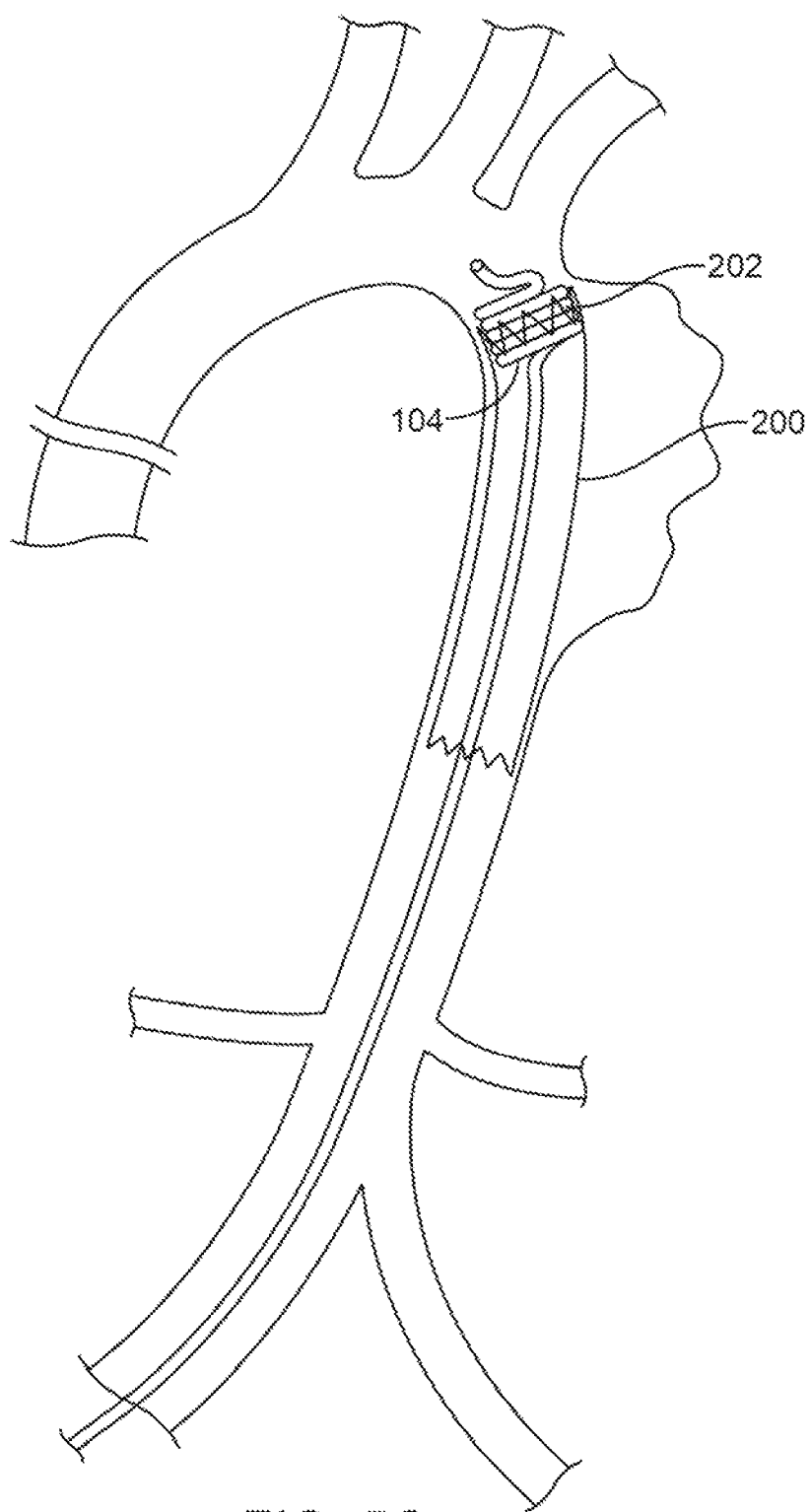

FIGS. 5A to 5C illustrate one example of a method of using a catheter 100 as described hereinks shown in FIG. 5A, a catheter 100 is advanced through a vessel 10 or organ in this variation the vessel comprises an aortic arch). However, the catheter 100 can be sized to fit various organs or vessels in the body. The catheter 100 can optionally be used to expand an implant 200 within the vessel 10. Alternatively, the catheter 100 can be used alone to provide an expansion force against the organ or vessel. FIG. 5B illustrates transformation of the deflectable section 104 of the catheter 100 into a helix. As shown, this can optionally partially expand the implant 202 for positioning or partial deployment. FIG. 5C shows expansion of the elastic material to fully deploy the implant 202. As described above, flow continues in the vessel 10 due to the passage in the helical shape.

FIG. 6A shows a variation of a device having a guide wire lumen 152 that extends through the device and has multiple openings 114 to allow a guidewire to pass outside of the deflectable section 104 and then reenter the device 100 at an opening 114 in the distal portion 102 so that the guidewire can pass through a distal guidewire opening 114. As shown, the guidewire lumen 152 can extend adjacent to a pull wire 108 or other similar means in the proximal portion 106 of the device 100. However, at or near the deflectable section 104, the guidewire lumen exits the device 100 at opening 114 so that the guidewire can exit the device along the deflectable section 104 and then reenter the device at a second opening 114 adjacent to the distal portion 102 of the device. This configuration allows the guidewire to extend out of the distal most opening 114.

FIG. 6B illustrates a guidewire 188 extending through the device 100 but passing through the helical turns 110. The guidewire 188 then re-enters the distal portion 102 of the device 100 so that a physician can navigate the distal portion 102 of the device 100 using the guidewire 188.

Figure 7A:
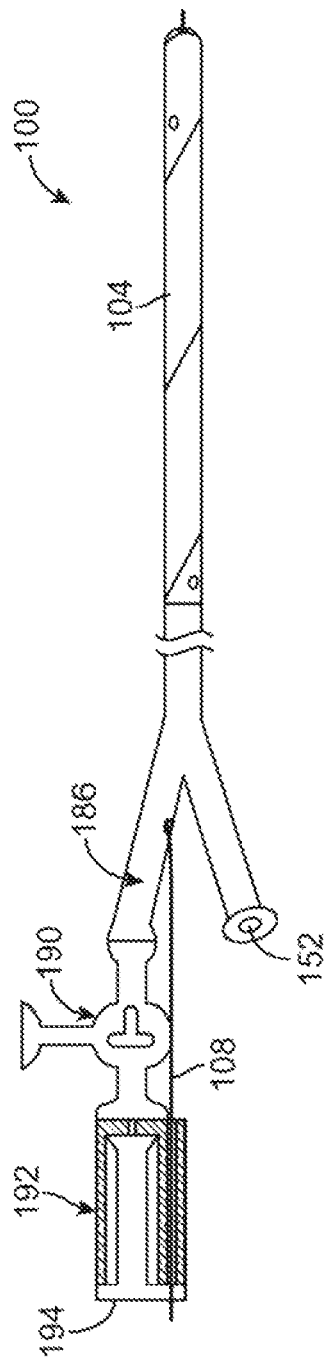
FIGS. 7A and 7B show another variation of a device having an actuator that allows for expansion of the deflectable section as it forms the helical turns.
Figure 7B:
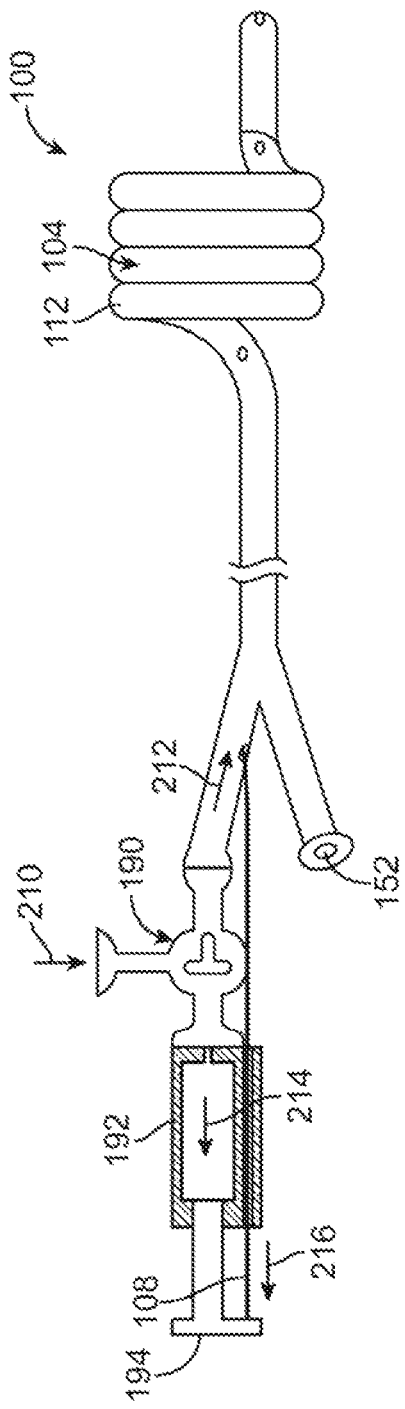

FIGS. 7A and 7B show another variation of a device 100 having an actuator 194 that allows for expansion of the deflectable section 104 as it forms the helical turns 112. FIG. 7A shows the device 100 in a linear configuration where a pull wire 108 that extends through the deflectable section 104 also extends proximally and is coupled to the actuator 192. In this variation, the pull wire 108 is coupled to a piston 194 in the actuator 192. The actuator 129 is also coupled to a valve 190 (in this variation the valve is a three way valve. The valve is also coupled to a fitting 186 of the device 100. It is noted that the pull wire 108 can be separate from the guide wire that is inserted through the guide wire lumen 152.

FIG. 7B represents a fluid source being driven through the valve 190 as represented by arrow 210. The fluid 210 travels through the device 100 as shown by arrow 212 to expand the expandable area as discussed above. However, the three way valve 190 also causes fluid to pressurize the actuator 192 to drive the piston 194 out of the actuator 192. Since the piston 194 is coupled to the pull wire 108, movement of the piston 194 causes proximal movement of the pull wire as noted by arrow 216. The movement of the pull wire causes the turns 112 of the deflectable section 104 to form the helical shape.

Figure 8A:
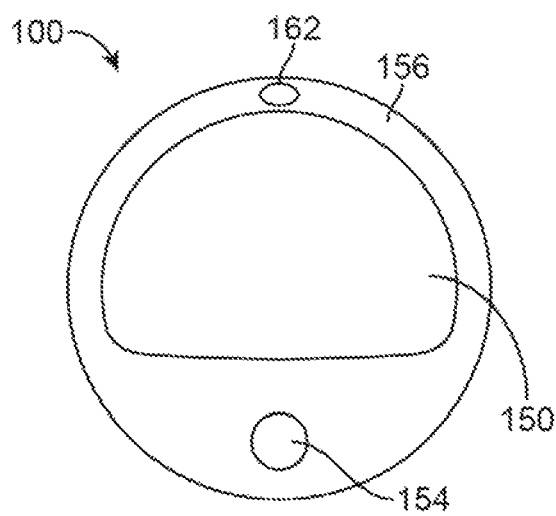
FIGS. 8A to 8D illustrate variations of devices having fluid delivery lumens.
Figure 8B:
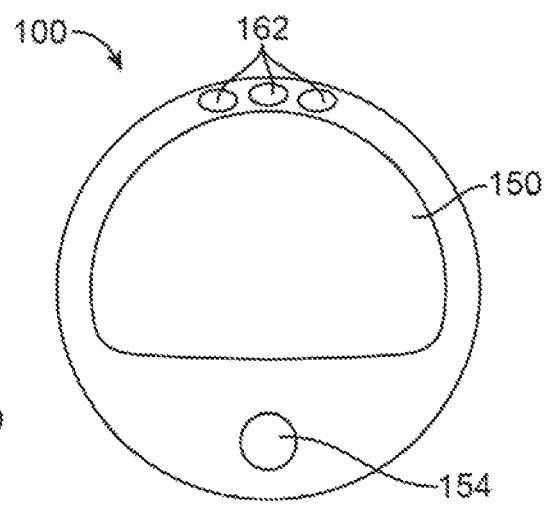
Figure 8C:
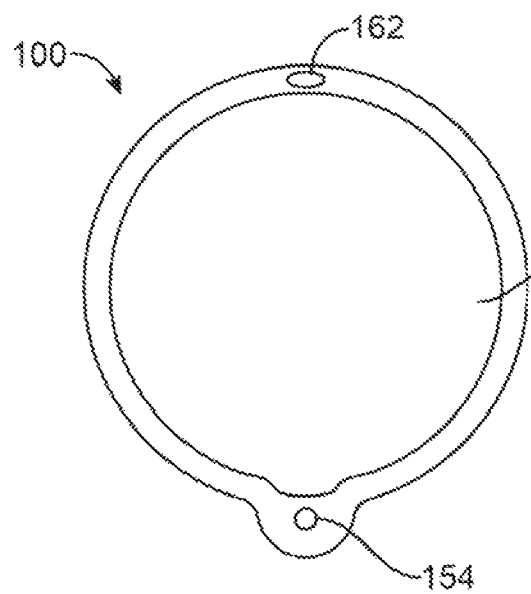
Figure 8D:
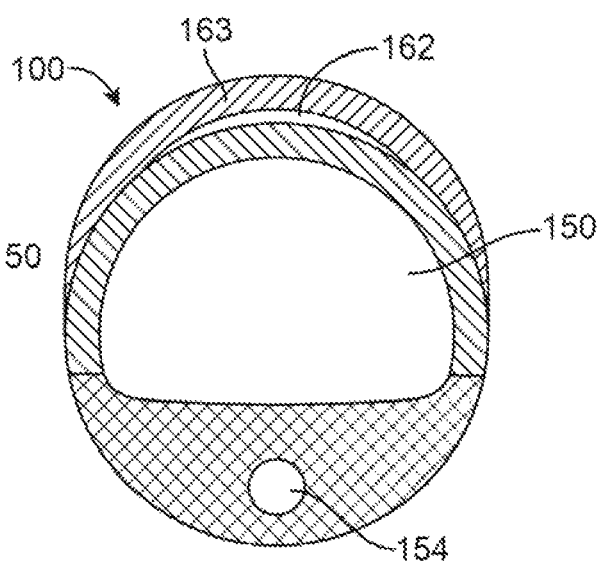

FIGS. 8A-8D illustrate another aspect for use with the devices described herein. The figures show a cross sectional view of an expandable section of the device 100. In this variation, the device 100 includes a fluid delivery lumen 162 that permits delivery of a fluid substance from the main body of the catheter. FIG. 8A shows a variation in which a fluid delivery lumen 162 is located in an expandable wall 156 of the device 100. Alternate variations allow for the fluid delivery lumen 162 to be positioned anywhere within the walls of the device 100. FIG. 8B illustrates a variation of the device 100 with a plurality of fluid delivery lumens 162. Although not depicted in FIGS. 8A-8D, the fluid delivery lumen 162 will have one or more ports that deposit the fluid at a desired location outside the device body 100. FIG. 8C show the device 100 in an expanded state where the fluid delivery lumen 162 assumes the shape of an oval without being occluded. FIG. 8D illustrates another variation of a device 100 where the fluid delivery lumen 162 is formed by an expandable section 163 on an exterior of the catheter 100. This configuration allows for a large fluid delivery lumen that can expand to facilitate passage of a fluid. The fluid delivery lumen 162 will have one or more fluid delivery ports (not shown in FIGS. 8A to 8D) that permit delivery of the fluid when the catheter is in the straight and/or coiled shape.

Figure 9A:
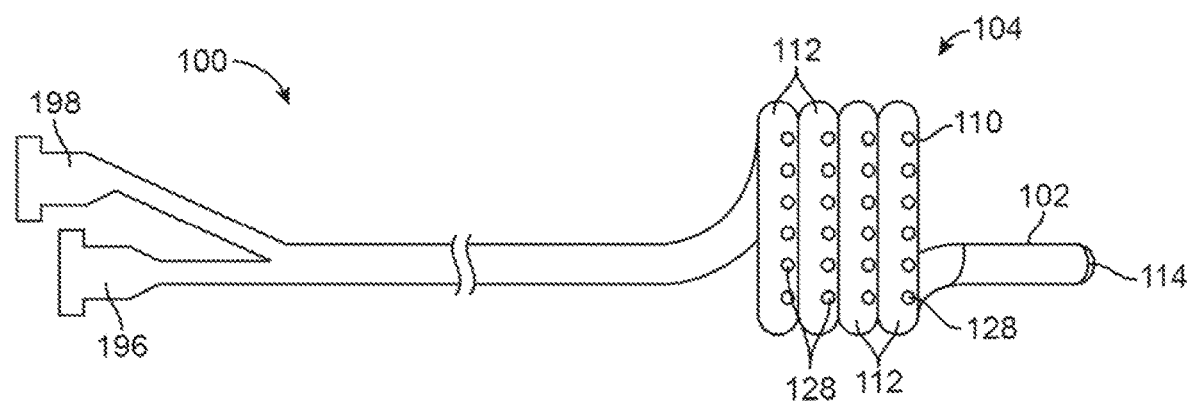
FIGS. 9A and 9B show ports on the exterior of the deflectable section.
Figure 9B:
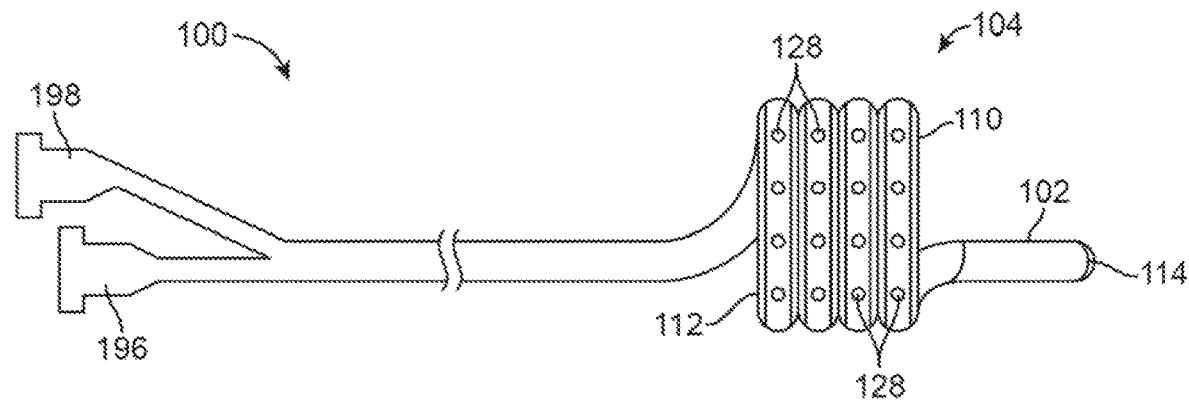

FIGS. 9A and 9B illustrate variations of a device as described herein where one or more fluid ports 128 terminate on an exterior surface of the coiled or helical portion of the device 100. The ports 128, which are in fluid communication with the fluid lumen, can be positioned on either side or both sides of the helical turn 112 of the deflectable section 104. In such a configuration, placing the ports 128 on the sides and/or inside of the helical turn 112 prevents the port 128 from being blocked during expansion of the deflectable section 104. FIG. 9B illustrates another variation of a device 100 having ports 128. In this variation, the ports 128 are positioned centrally on the turns 128 of the deflectable section 104. FIGS. 9A and 9B also show the device 100 having any number of hubs 196, 198 that can be fluidly coupled to the fluid delivery lumen (not shown) such that an external source of fluid can be coupled to the respective hub allowing for delivery of the fluid. In additional variations, the ports can be located on additional portions of the catheter, including but not limited to, the non-expanding portion of the catheter.

Figure 10:
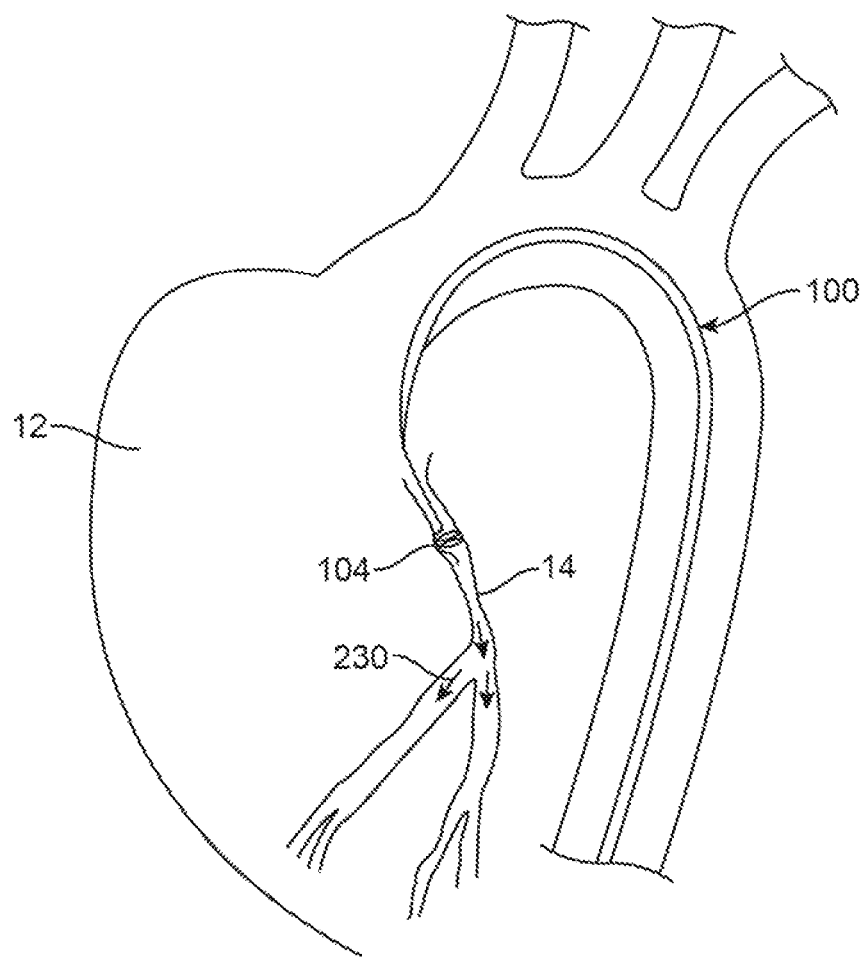
FIG. 10 shows a variation of a device expanded in an artery and delivering a fluid.

FIG. 10 illustrates a variation of the device 100 described herein positioned into a coronary artery 14 on a heart 12 where the deflectable section 104 is coiled while allowing blood flow through the coronary vessel 14. The device 100 also permits delivery of drugs, medicine or other agents through the ports described above.

Figure 11A:
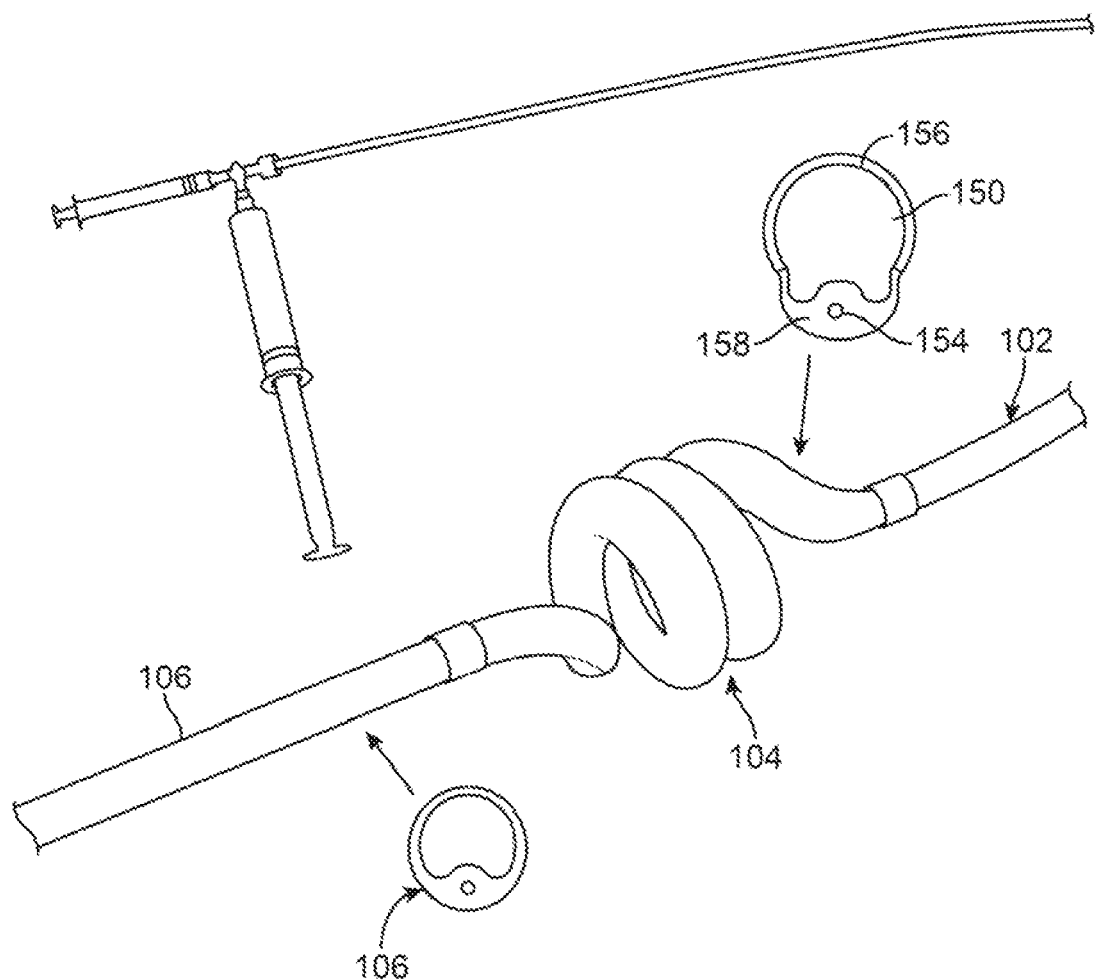
FIGS. 11A and 11B show additional variations of the device.
Figure 11B:
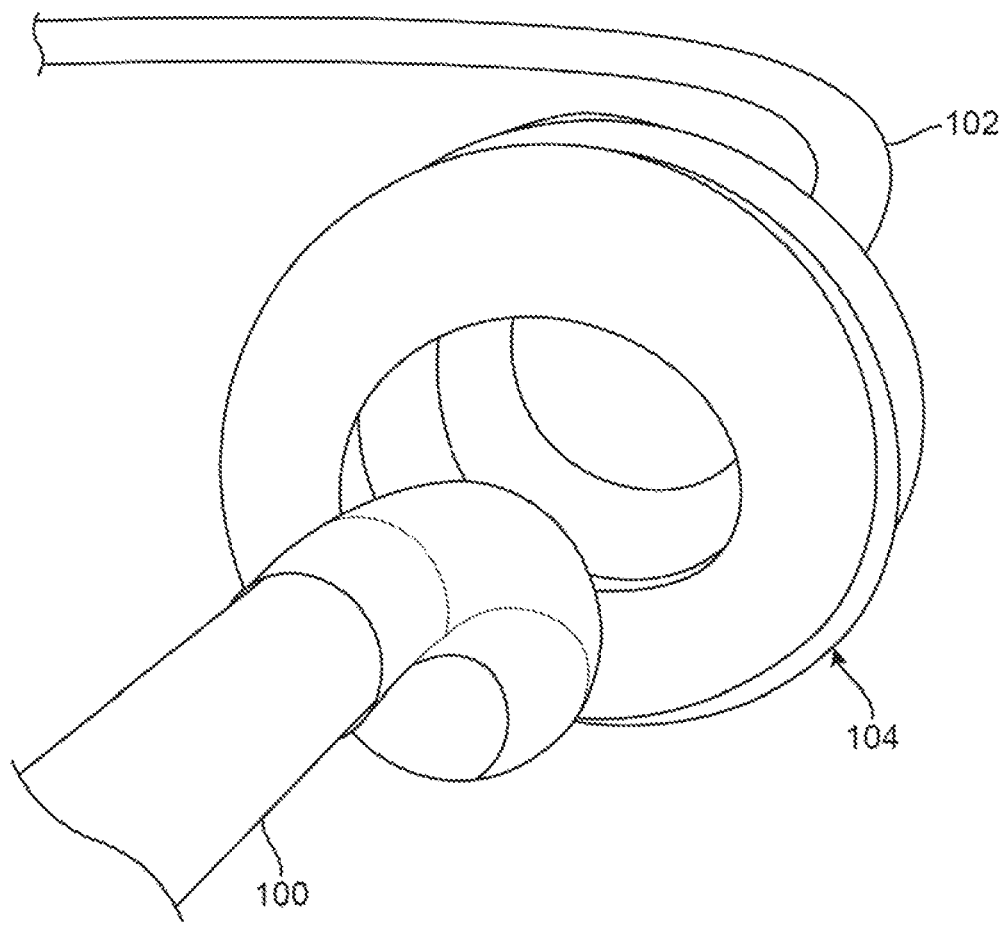

FIGS. 11A and 11B show additional variations of the device where the helical or deflectable section is joined to a proximal portion 106 and a distal portion 102 such that the deflectable section comprises an elastic material 156 and a flexible material 158 to allow deformation into a helical shape. As shown, the deflectable section 104 can optionally selected to be a clear or semi-clear material.

The devices described above can address a common problem when common practice of using a soft wire to gain access to target location and then bringing a more supportive guide catheter over the wire can either lead to the guidewire. In such cases, the stiffer instrument backs out from the desired target location. For example, a variation of the device can use uses the floppy tip trackable helical balloon catheter to easily track over the soft guidewire which has been brought to the target location and then the outer balloon is inflated to engage the wall of the artery while allowing blood flow past the inflated device to continue perfusion of the downstream organs. An internal balloon can be inflated which impinges on the IL) of the Python helical balloon catheter at the distal tip RX portion of the helical balloon catheter such that when the guidewire is residing in the RX lumen it is held fixed in place by the inflated internal balloon. This effectively allows for traction to be applied to the guidewire (pulling on the guidewire does not move the tip of the Quidewire) because the outer helical balloon is engaged to the ID of the blood vessel or bronchial lumen which transfers the tension force to the artery, vein, or lumen.

Figure 12A:
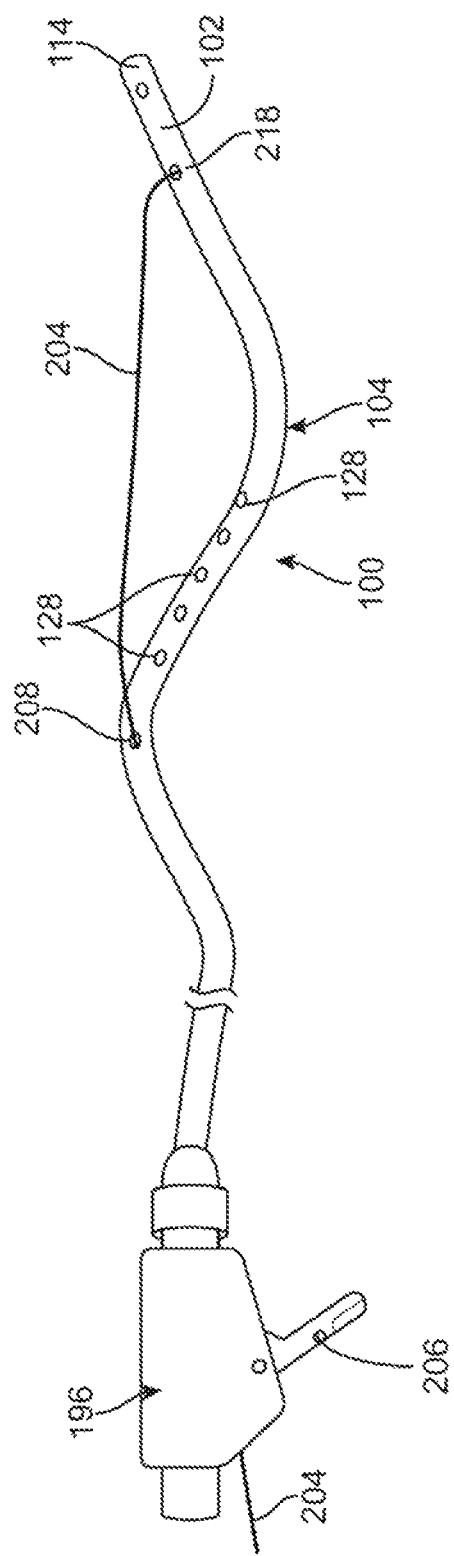
FIGS. 12A to 12D show a variation of a device with an addition wire or suture used to assist the deflectable section when forming a coil or helix.
Figure 12B:
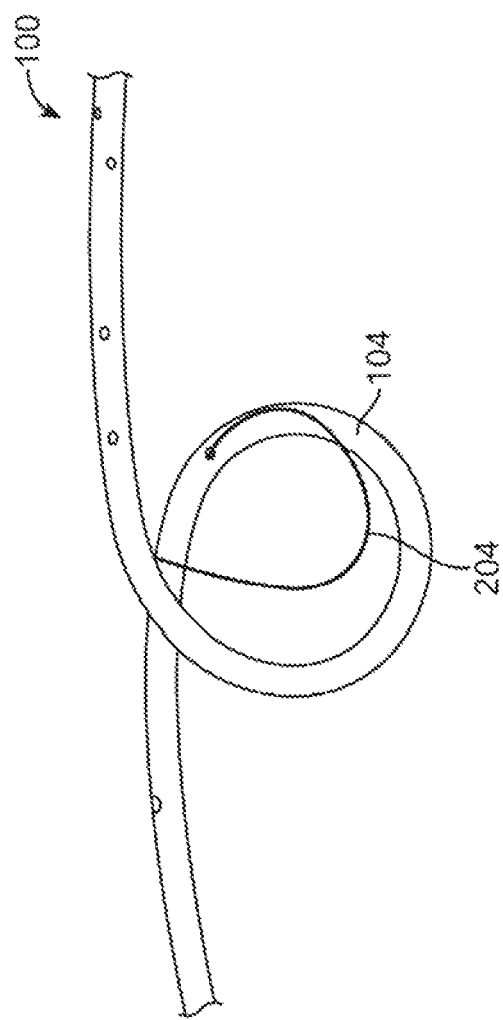

FIGS. 12A to 12B show an example of a device 100 having a feature that aids in the formation of the deflectable section 104 into a helical structure. As with the other variations described herein, the features and aspects of each example discussed herein can be combined with other disclosed variations of the device where such features do not conflict.

As shown in FIG. 12A, the device 100 includes a wire 204 (which can be a wire, suture, thread, strand or similar structure) that extends from a proximal end of the device 100 (e.g., through a hub 196 as shown) to a first opening 208 that is located proximally to (or on a proximal end) of the deflectable section 104. The wire 204 extends outside of the device along a portion of the deflectable section 104 and re-enters the device 100 a location 218 distal to (or at a distal end of) the deflectable section 104. The wire 204 can be fixed at the distal location 218 or can be free floating as long as it can remain within the device a the distal opening 218. FIG. 12A also illustrates this variation of the device 100 as having a hub 196 with a locking feature 206. The locking feature 206 secures the wire 204 when desired. As discussed below, once the deflectable section is positioned as desired, the wire 204 can be locked into place using the locking feature 206 to secure the helical shape of the deflectable section. In an additional variation, the wire 204 can be coupled to a piston mechanism as described in FIGS. 7A and 7B above.

Figure 12C:
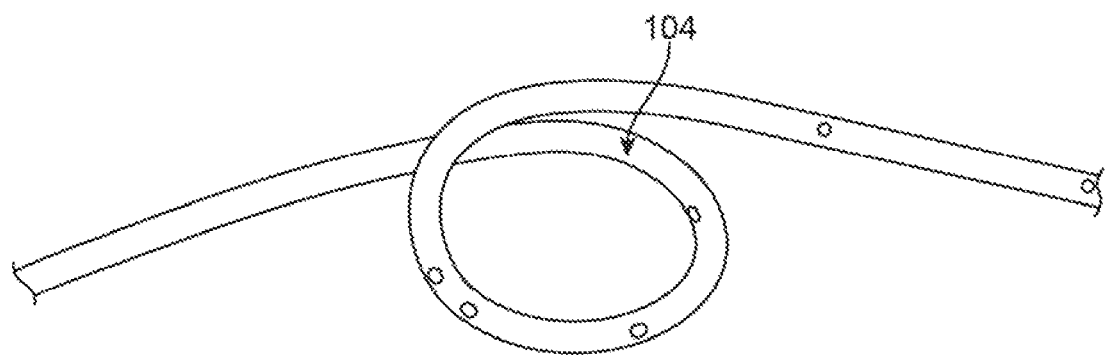
Figure 12D:
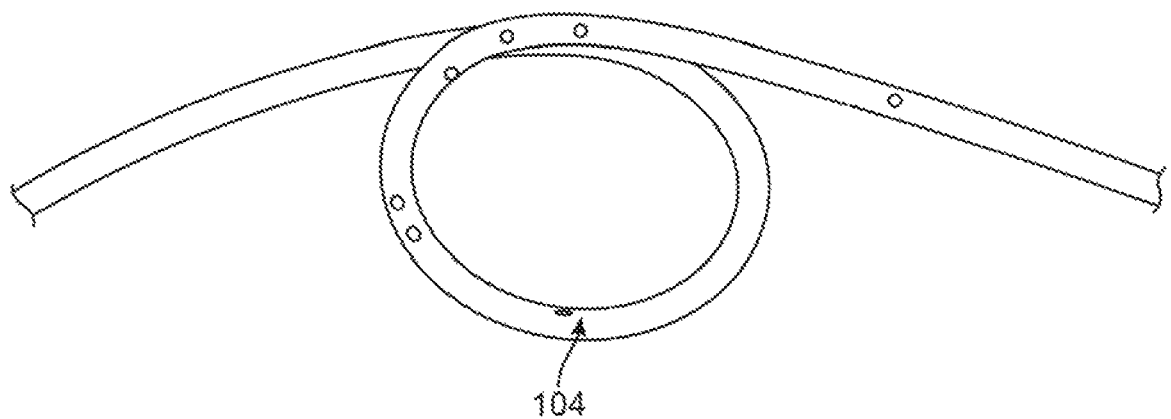

FIG. 12B illustrates the deflectable section 104 as it starts to coil. As mentioned above, the deflectable section 104 can being to assume a coil shape using a pull wire or the natural characteristics of the materials forming the device 100. As shown, the wire 204 remains exterior to the device 100. FIG. 12C illustrates the wire 204 being drawn to dose the distance between the proximal opening 208 and the distal opening 218. This action permits the deflectable section 104 of the device 100 to form a coiled shape as desired. FIG. 12D illustrates the helical shape of the deformable section 104 when the wire (not shown) secures the helical coil of the device. Although the variation depicted in FIGS. 12A to 12D only coils a single turn of the helical shape, any number of wires can be used to form additional turns of the device. Alternatively, a wire can pass through any number of turns of the deflectable section 104.

In another variation, the device can include a string or other similar member that is attached at a proximal end of the distal tip and extends through the pullwire lumen exiting just where the first balloon loop starts. Then when the catheter forms its first loop, the string goes back into the lumen. This could be repeated depending on the number of loops of the balloon. When the catheter is straight before inflation, the string is external for a few inches at either one spot along the length of catheter at the loop section, or two spots if it had two loops. The string can be pulled from the back either manually or with the syringe plunger concept that di disclosed above.

Such a variation of the device described herein can provide traction to support a guidewire guide catheter, or similar instrument at a distal or remote location within vasculature or other tortuous anatomy such as a bronchial passage. Providing traction support for the instrument allows for tracking/advancing of a stiller device over the instrument than would otherwise be possible. For example, FIG. 13A illustrates an example of a conventional catheter 140 being tracked over a guide wire 142 through tortuous anatomy. As noted above, the device can be used in any tortuous anatomy not limited to the vasculature. FIG. 13A shows a portion 144 of the catheter/guidewire forming an undesired path as illustrated by the bowed out section. Typically, such a situation occurs when a relatively stiff device advances over the guidewire or through the guide catheter. Continued advancement can cause the catheter 140 and/or guidewire 142 to back out of the target location within the vessel. Again, such a situation can commonly occur when advancing a stem delivery catheter or other relatively stiffer instrument/device along the guidewire and/or through the catheter.

FIG. 13B illustrates a device 100 as described above where a helical portion 110 can be used w anchor the device at an appropriate target while permitting blood flow through the helical portion 110. In this variation, the device 100 is configured to apply traction on the guidewire 188 at a distal portion 102 of the device 100. Application of traction on the guidewire 188 permits a tensile force 146 to be applied on the guidewire 188. This added tension allows relatively stiffer devices to be advanced along the quidewire/device 100 (in those cases where the guidewire 188 advances through the device 100) without the stiffer device causing distortion of the guidewire/catheter as shown FIG. 13A.

Figure 14A:
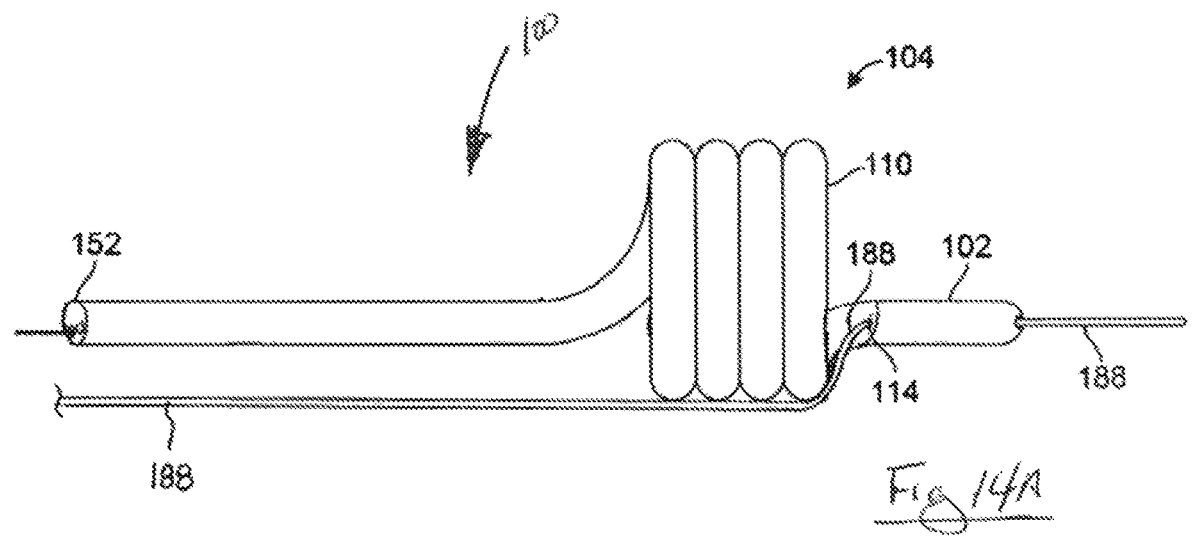
FIGS. 14A to 14C illustrate an example of a helical balloon catheter configured to apply compression or clamping to a guidewire.

FIG. 14A illustrates an example of a device 100 that can apply compression to a guidewire 188 permitting the guidewire to be placed in a state of traction. FIG. 14A illustrates a guidewire 188 extending through a distal portion 102 of the deflectable section 104 of the device and exterior to a remainder of the device 100. However, alternate designs contemplate the guide wire extending through an entirety or an increased portion of the device 100 as shown above.

Figure 14B:
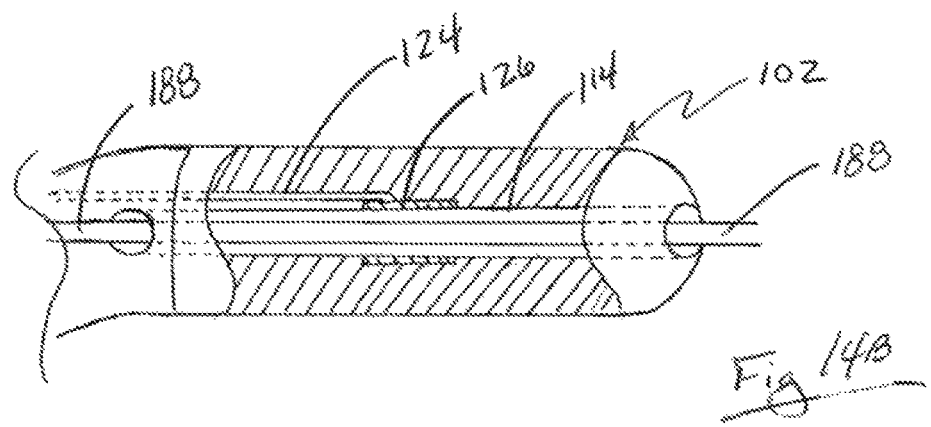
Figure 14C:
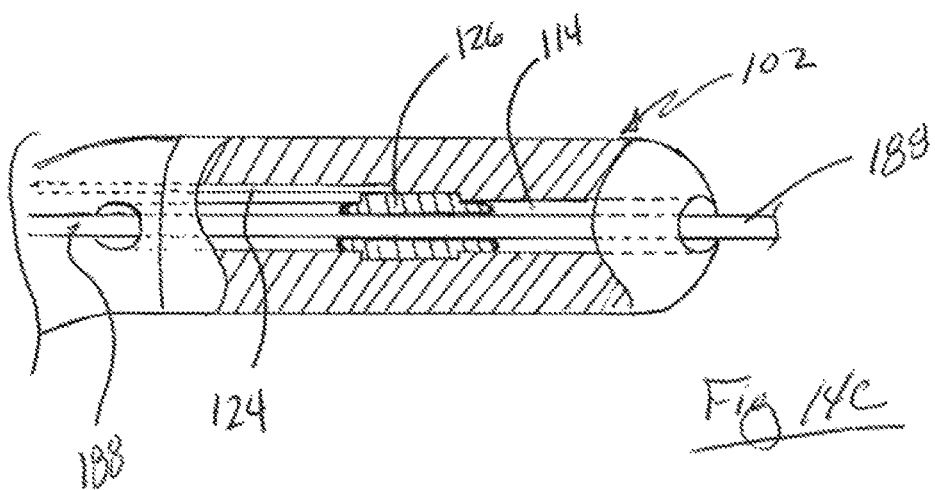

FIG. 14B illustrates a partial cross sectional view of a distal portion 102 of the deflectable section 104 of the device 100. As shown, the guide wire 188 passes through a guidewire lumen 114. The interior of the guide wire lumen 114 includes an expandable balloon, bladder, or other expandable structure 126 that is fluidly coupled to an expansion lumen 126 (or a conductive electrical path in the event that the expandable structure 126 is electromechanical and/or electrically triggered. FIG. 14B illustrates a condition where the expandable structure 126 is in an unexpanded profile. FIG. 14C illustrates a condition where the expandable structure 126 is expanded to enter the guidewire lumen 114 and apply a compressive/clamping force upon the guidewire 188. The expandable member 126 can extend as show in FIG. 14C. Alternatively, the expandable member 126 can extend through the length of the lumen. In another variation, the expandable member can comprise a wedge based structure that impinges the guidewire on one or more sides.

In any event, actuation of the expandable member 126 prevents the guidewire from moving through the lumen 114, which allows the medical practitioner to apply tension on the guidewire to place the guidewire in a state of traction. In certain variations, the distal portion 102 of the device 100 can remain relatively stiff or rigid to prevent lateral movement of the clamped member upon the application of tension to the clamped guidewire.

Basically, this variation can assist with problem of undesired loss of position for guidewires and catheters that are located at a targets within the vascular, bronchial tree, or other tortuous anatomy. These devices serve as a guide to track other therapeutic or diagnostic devices to the target location over the guidewire or through the guide catheter. Typically a soft tip guidewire is first driven to the target location from a remote access point and its distal flexibility and proximal stiffness allows for navigation around corners and even allows for reversing the direction such as when a guidewire or catheter enters the body at the location of the femoral artery and is placed in an innominate artery that extends from a type 111 aortic arch. This anatomical consideration is one predictor of the difficulty of carotid stenting as is well known by those skilled in the art.

I claim:

1. A catheter for use with a guidewire, the catheter comprising:
   a proximal portion, a distal portion, and a deflectable section located therebetween, the deflectable section having a deflectable cross section;
   where the deflectable cross section comprises an elastic material on a first side and a flexible support material on a second side, an inflation lumen bounded by both the elastic material and the flexible support material, and where the deflectable cross section rotates along a length of the deflectable section such that the elastic material, the inflation lumen, and the flexible support material extend helically along the length of the deflectable section;
   a pull wire extending through the flexible support material at least along the length of the deflectable section and at least to the proximal portion of the catheter, such that proximal tension applied to the pull wire causes the deflectable section to deflect into a helical profile;
   a guidewire lumen extending through the distal portion, the guidewire lumen having an actuatable structure located within the guidewire lumen to occlude the guidewire lumen, such that when the guidewire is located within the guidewire lumen, actuation of the actuatable structure occludes the guidewire lumen to apply a compressive force against the guidewire;
   wherein when a pressure within the inflation lumen increases, the elastic material expands away from the inflation lumen.

2. The catheter of claim 1, wherein in the helical profile, the flexible support material is located along an internal diameter of the helical profile and the elastic material is located on an external diameter of the helical profile such that upon increasing the pressure within the inflation lumen, the elastic material expands radially outward.

3. The catheter of claim 2, where the guidewire lumen extends through a center of the proximal portion, the distal portion, and the deflectable section.

4. The catheter of claim 2, where when the guidewire is located within the guidewire lumen and the actuatable structure is actuated, the guidewire extends through a distal portion of the guidewire lumen.

5. The catheter of claim 1, where the pull wire extends through a pull wire lumen and where the pull wire lumen and inflation lumen are located 180 degrees opposite in the deflectable cross section.

6. The catheter of claim 1, further comprising the guidewire lumen further extending through the proximal portion and the flexible support material of the deflectable section.

7. The catheter of claim 1, where the inflation lumen also extends through the proximal portion, or where a flexible support material durometer is less than a proximal portion durometer, or where the helical profile comprises at least one turn.

8. The catheter of claim 1, where the helical profile comprises a plurality of turns and the helical profile has a pitch and a diameter.

9. The catheter of claim 8, where at least two turns of the plurality of turns is contiguous along a length of the helical profile, or where at least another two turns of the plurality of turns are spaced and do not touch along a length of the helical profile, or where the pitch of the helical profile is consistent for the plurality of turns, or where the pitch of the helical profile varies for the plurality of turns, or where the diameter of the helical profile is consistent along a length of the helical profile, or where the diameter of the helical profile varies along a length of the helical profile.

10. The catheter of claim 1, where the actuatable structure directly contacts the guidewire when actuated.

11. The catheter of claim 1, where the actuatable structure extends into the guidewire lumen when actuated.

12. The catheter of claim 1, where when the guidewire is in the guidewire lumen in the distal portion of the catheter, the guidewire enters the distal portion of the catheter proximal to the actuatable structure and exits the distal portion of the catheter distal to the actuatable structure.

13. The catheter of claim 1, where actuation of the actuatable structure occludes the guidewire lumen to apply a compressive force against the guidewire such that traction applied to the guidewire permits a tensile force to be applied on the guidewire to allow a device to be tracked or advanced over the guidewire without the device causing distortion of the guidewire or of the catheter.

14. The catheter of claim 1, where actuation of the actuatable structure occludes the guidewire lumen to apply a compressive force against the guidewire such that the guidewire is placed in a state of traction when tension is applied to the guidewire.

15. The catheter of claim 1, where when the deflectable section has the helical profile, the actuatable structure is distal to the helical section.

16. The catheter of claim 1, where when the deflectable section has the helical profile, the helical profile defines a passage through a center of the helical profile, and where when the deflectable section has the helical profile, the actuatable structure extends distally away from the passage.

17. The catheter of claim 1, where when the deflectable section has the helical profile, the helical profile is configured to anchor the expandable structure in place.

18. The catheter of claim 1, where when the deflectable section has the helical profile and when the expandable structure is in an actuated state, the catheter defines a lumen through a center region of the helical profile.

19. The catheter of claim 1, where when the deflectable section has the helical profile, when the expandable structure is in an actuated state, and when the guidewire is in a state of traction, a device is advanceable over the guidewire such that the guidewire in the state of traction inhibits the device from causing distortion of the guidewire as the device is advanced over the guidewire.

20. The catheter of claim 19, where the device is advanceable over the guidewire along the outside of the catheter.

\* \* \* \* \*